(12) United States Patent
Zhao et al.

(10) Patent No.: US 10,273,198 B2
(45) Date of Patent: Apr. 30, 2019

(54) SOLVENT EXCHANGER AND METHOD FOR IMPROVING THE EXCHANGE EFFICIENCY OF CTA SOLVENT

(71) Applicant: TIANHUA INSTITUTE OF CHEMICAL MACHINERY AND AUTOMATION CO., LTD, Gansu (CN)

(72) Inventors: Xu Zhao, Gansu (CN); Wanyao Zhang, Gansu (CN); Zhongxin Sun, Gansu (CN); Yongpeng Tan, Gansu (CN); Xiangnan Zhai, Gansu (CN); Tianbao Wang, Gansu (CN); Yuanyue Liang, Gansu (CN); Guohai Zhang, Gansu (CN); Xiaopeng Feng, Gansu (CN); Yanshun Shen, Gansu (CN)

(73) Assignee: TIANHUA INSTITUTE OF CHEMICAL MACHINERY AND AUTOMATION CO., LTD, Gansu (CN)

( * ) Notice: Subject to any disclaimer, the term of this patent is extended or adjusted under 35 U.S.C. 154(b) by 214 days.

(21) Appl. No.: 15/305,034

(22) PCT Filed: Jan. 9, 2015

(86) PCT No.: PCT/CN2015/070410
§ 371 (c)(1),
(2) Date: Oct. 18, 2016

(87) PCT Pub. No.: WO2015/161684
PCT Pub. Date: Oct. 29, 2015

(65) Prior Publication Data
US 2017/0183285 A1    Jun. 29, 2017

(30) Foreign Application Priority Data
Apr. 24, 2014 (CN) .......................... 2014 1 0166210

(51) Int. Cl.
*C07C 51/48* (2006.01)
*B01D 33/76* (2006.01)
(Continued)

(52) U.S. Cl.
CPC .............. *C07C 51/48* (2013.01); *B01D 33/11* (2013.01); *B01D 33/39* (2013.01); *B01D 33/76* (2013.01); *C07C 51/42* (2013.01); *C07C 63/26* (2013.01)

(58) Field of Classification Search
CPC ......... C07C 51/48; C07C 51/42; C07C 63/26; B01D 33/76; B01D 33/39; B01D 33/11
See application file for complete search history.

(56) References Cited

U.S. PATENT DOCUMENTS 5,200,557 A * 4/1993 Gee .......................... C07C 51/43
562/414
5,583,254 A * 12/1996 Turner .................... C07C 51/43
562/414
(Continued)

FOREIGN PATENT DOCUMENTS

CN          1150945 A     6/1997
CN        101045683 A    10/2007
(Continued)

OTHER PUBLICATIONS

Zhao (CN 103387492). Machine translation and original attached (Year: 2013).*
(Continued)

*Primary Examiner* — Katherine Zalasky
*Assistant Examiner* — Liam Royce
(74) *Attorney, Agent, or Firm* — Muncy, Geissler, Olds & Lowe, P.C.

(57) ABSTRACT

A solvent exchanger and a method is provided for: pressurizing a CTA slurry into a solvent exchanger for separation
(Continued)

and obtaining a mother liquor, a bias flow mother liquor and a suspended matter A; washing the suspended matter A to obtain a primary filtrate, a bias flow primary filtrate and a suspended matter B; washing the suspended matter B to obtain a secondary filtrate, a bias flow secondary filtrate and a suspended matter C; washing the suspended matter C to obtain a tertiary filtrate, a bias flow tertiary filtrate and a suspended matter D; washing the suspended matter D to obtain a fourth filtrate, a bias flow fourth filtrate and a suspended matter E; washing the suspended matter E to obtain a fifth filtrate, a bias flow fifth filtrate and a filter cake; and after finished, back-flushing the filter cake and then pulping to obtain a slurry, and discharging.

3 Claims, 3 Drawing Sheets

(51) Int. Cl.
*B01D 33/39* (2006.01)
*B01D 33/11* (2006.01)
*C07C 63/26* (2006.01)
*C07C 51/42* (2006.01)

(56) References Cited

U.S. PATENT DOCUMENTS

| | | | |
|---|---|---|---|
| 8,697,906 B2 * | 4/2014 | Parker | C07C 51/47 |
| | | | 562/474 |
| 2015/0182890 A1 * | 7/2015 | Keyes | B01D 33/60 |
| | | | 562/485 |

FOREIGN PATENT DOCUMENTS

| | | | |
|---|---|---|---|
| CN | 102381964 A | 3/2012 | |
| CN | 102476994 A | 5/2012 | |
| CN | 102992999 A | 3/2013 | |
| CN | 103387492 A | 11/2013 | |
| CN | 103936581 A | 7/2014 | |
| DE | 878795 C * | 10/1953 | B01D 33/073 |

OTHER PUBLICATIONS

Fest (DE 878795) machine translation and original attached (Year: 1953).*

* cited by examiner

SOLVENT EXCHANGER AND METHOD FOR IMPROVING THE EXCHANGE EFFICIENCY OF CTA SOLVENT

FIELD OF THE INVENTION

The invention relates to the technical field of exchange of CTA (Crude Terephthalic acid) solvent in an oxidation unit during production and preparation of PTA (Pure terephthalic acid), and in particular to a solvent exchanger and a method for improving the exchange efficiency of a CTA solvent.

DISCUSSION OF THE RELATED ART

PTA is a major raw material for producing polyester fiber, resin, film and container resin, and widely applied in such fields as chemical fiber, container, packaging and film production. In recent years, PTA process develops rapidly, and solvent exchange technology develops quickly therewith. With the solvent exchange technology, the filtration, drying, pneumatic delivery and storage of CTA in the PTA oxidation device can be completed by a "solvent exchange" unit simply. The CTA solvent exchange technology is of multi-stage countercurrent washing process. Clean washing liquor enters a solvent exchanger from the washing section at the last stage, and is discharged into a corresponding chamber of a control head through a filtrate pipeline upon solvent exchange completes, and then discharged into a corresponding filtrate tank. The filtrate in the filtrate tank is pumped into a washing section at an upper stage of the solvent exchanger to continue solvent exchange, so that the washing is performed forwardly stage by stage in a flow direction opposite to the filter cake. The method has been granted as a Chinese patent (No. 201010571736.6) in the name of Tianhua Institute of Chemical Machinery & Automation Co., Ltd. However, the method is only an implementation method designed based on the ideal conditions. During operations of the pressure filtering, washing and separating units by using a drum and multiple-chambers in a CTA solvent exchanger, as the residual liquor in the filtrate pipeline of the pressure filtering, washing and separating units by using a drum and multiple-chambers cannot be discharged in time, the residual liquor will enter the cleaner washing section at the next stage along with rotation of the equipment, which increases concentration of the solvent in the washing liquor at the next stage, largely reducing the solvent exchange efficiency.

SUMMARY

A technical problem to be solved by the invention is to provide a solvent exchanger capable of improving the exchange efficiency of a CTA solvent.

In order to solve the problem, the solvent exchanger of the invention comprises a frame and a control head; the frame is divided into a feeding section, a primary washing unit chamber, a secondary washing unit chamber, a tertiary washing unit chamber, a fourth washing unit chamber, a fifth washing unit chamber and an unloading section II by a separation block A, a separation block B, a separation block C, a separation block D, a separation block E, a separation block F and a separation block G. The control head is divided into a mother liquor chamber, a primary filtrate chamber, a secondary filtrate chamber, a tertiary filtrate chamber, a fourth filtrate chamber, a fifth filtrate chamber and an unloading section I by a separation block a, a separation block b, a separation block c, a separation block d, a separation block e, a separation block f and a separation block g. The separation block A, the separation block B, the separation block C, the separation block D, the separation block E, the separation block F and the separation block G are in one-to-one correspondence to the separation block a, the separation block b, the separation block c, the separation block d, the separation block e, the separation block f and the separation block g. An adjusting plate is arranged on the control head. A drainage opening is arranged at the end of the fifth filtrate chamber. The primary washing unit chamber, the secondary washing unit chamber, the tertiary washing unit chamber, the fourth washing unit chamber and the fifth washing unit chamber are respectively connected with the primary filtrate chamber, the secondary filtrate chamber, the tertiary filtrate chamber, the fourth filtrate chamber and the fifth filtrate chamber by the filtrate pipeline in a one-to-one correspondence manner.

Another technical problem to be solved by the invention is to provide a method for improving the exchange efficiency of a CTA solvent and capable of achieving the purpose of low energy consumption.

In order to solve the problem, a method for improving the exchange efficiency of a CTA solvent of the invention comprises the following steps:

(1) pressurizing, by a slurry pump, a CTA slurry in a CTA slurry tank into a solvent exchanger, and passing the CTA slurry through a feeding section in a frame of the solvent exchanger to a filter unit chamber for separation to obtain a mother liquor, a bias flow mother liquor and a suspended matter A respectively; passing the mother liquor and the bias flow mother liquor through a mother liquor chamber in a control head of the solvent exchanger to a mother liquor tank, and discharging the mother liquor and the bias flow mother liquor by a mother liquor pump connected with the mother liquor tank, wherein the bias flow mother liquor is from the residual mother liquor in a filtrate pipeline; adjusting position of a separation block a between the mother liquor chamber and a primary filtrate chamber to allow the separation block a to lead a separation block A of the corresponding frame by an angle $\theta_1$, and the residual mother liquor to enter the corresponding mother liquor chamber within the time of rotation of a drum by the angle $\theta_1$;

(2) after filling the filter unit chamber with the suspended matter A, pressurizing, by a primary washing water pump, the washing water stored in a primary washing water tank into a primary washing unit chamber in the frame, and conveying the suspended matter A into the primary washing unit chamber for washing to obtain a primary filtrate, a bias flow primary filtrate and a suspended matter B respectively; passing the primary filtrate and the bias flow primary filtrate through the primary filtrate chamber in the control head to a primary filtrate tank, and discharging the primary filtrate and the bias flow primary filtrate by a primary filtrate pump connected with the primary filtrate tank; wherein the washing water in the primary washing water tank is from a secondary filtrate and a bias flow secondary filtrate discharged from a secondary washing unit chamber, and the bias flow primary filtrate is from the residual primary filtrate in the filtrate pipeline; adjusting position of a separation block b between the primary filtrate chamber and a secondary filtrate chamber to allow the separation block b to lead a separation block B of the corresponding frame by an angle $\theta_2$, and the residual primary filtrate to enter the corresponding primary filtrate chamber within the time of rotation of the drum by the angle $\theta_2$;

(3) after filling the primary washing unit chamber with the suspended matter B, pressurizing, by a secondary washing water pump, the washing water stored in a secondary washing water tank into a secondary washing unit chamber in the frame; with the rotation of the drum, conveying the suspended matter B into the secondary washing unit chamber for washing to obtain a secondary filtrate, a bias flow secondary filtrate and a suspended matter C respectively; passing the secondary filtrate and bias flow secondary filtrate through the secondary filtrate chamber in the control head to a secondary filtrate tank, and conveying the secondary filtrate and bias flow secondary filtrate into the solvent exchanger by a secondary filtrate pump connected with the secondary filtrate tank, wherein the washing water in the secondary washing water tank is from a tertiary filtrate and a bias flow tertiary filtrate discharged from a tertiary washing unit chamber, and the bias flow secondary filtrate is from the residual secondary filtrate in the filtrate pipeline; adjusting position of a separation block c between the secondary filtrate chamber and a tertiary filtrate chamber to allow the separation block c to lead a separation block C of the corresponding frame by an angle θ3, and the residual secondary filtrate to enter the corresponding secondary filtrate chamber within the time of rotation of the drum by the angle θ3;

(4) after filling the secondary washing unit chamber with the suspended matter C, pressurizing, by a tertiary washing water pump, the washing water stored in a tertiary washing water tank into a tertiary washing unit chamber in the frame; with the rotation of the drum, conveying the suspended matter C into the tertiary washing unit chamber for washing to obtain a tertiary filtrate, a bias flow tertiary filtrate and a suspended matter D respectively; passing the tertiary filtrate and bias flow tertiary filtrate through the tertiary filtrate chamber in the control head to a tertiary filtrate tank, and conveying the tertiary filtrate and bias flow tertiary filtrate into the solvent exchanger by a tertiary filtrate pump connected with the tertiary filtrate tank, wherein the washing water in the tertiary washing water tank is from a fourth filtrate and a bias flow fourth filtrate discharged from a fourth washing unit chamber, and the bias flow tertiary filtrate is from the residual tertiary filtrate in the filtrate pipeline; adjusting position of a separation block d between the tertiary filtrate chamber and a fourth filtrate chamber to allow the separation block d to lead a separation block D of the corresponding frame by an angle θ4, and the residual tertiary filtrate to enter the corresponding tertiary filtrate chamber within the time of rotation of the drum by the angle θ4;

(5) after filling the tertiary washing unit chamber with the suspended matter D, pressurizing, by a fourth washing water pump, the washing water stored in a fourth washing water tank into a fourth washing unit chamber in the frame; with the rotation of the drum, conveying the suspended matter D into the fourth washing unit chamber for washing to obtain a fourth filtrate, a bias flow fourth filtrate and a suspended matter E respectively; passing the fourth filtrate and bias flow fourth filtrate through the fourth filtrate chamber in the control head to a fourth filtrate tank, and conveying the fourth filtrate and bias flow fourth filtrate into the solvent exchanger by a fourth filtrate pump connected with the fourth filtrate tank, wherein the washing water in the fourth washing water tank is from a fifth filtrate and a bias flow fifth filtrate discharged from a fifth washing unit chamber, and the bias flow fourth filtrate is from the residual fourth filtrate in the filtrate pipeline; adjusting position of a separation block e between the fourth filtrate chamber and a fifth filtrate chamber to allow the separation block e to lead a separation block E of the corresponding frame by an angle θ5, and the residual fourth filtrate to enter the corresponding fourth filtrate chamber within the time of rotation of the drum by the angle θ5;

(6) after filling the fourth washing unit chamber with the suspended matter E, pressurizing, by a fifth washing water pump, the washing water stored in a fifth washing water tank into a fifth washing unit chamber in the frame; with the rotation of the drum, conveying the suspended matter E into the fifth washing unit chamber for washing to obtain a fifth filtrate, a bias flow fifth filtrate and a filter cake respectively; passing the fifth filtrate through the fifth filtrate chamber in the control head to a fifth filtrate tank, and conveying the fifth filtrate into the solvent exchanger by a fifth filtrate pump connected with the fifth filtrate tank, wherein the bias flow fifth filtrate is from the residual fifth filtrate in the filtrate pipeline; guiding, by a suction machine unit, the bias flow fifth filtrate from a drainage opening to a bias flow filtrate tank through the fifth filtrate chamber, and conveying the bias flow fifth filtrate into the fifth filtrate tank by a bias flow filtrate pump connected with the bias flow filtrate tank, wherein an outlet of the suction machine unit is connected with a pulping tank, and the washing water in the fifth washing water tank is from fresh water heated to 90° C.; and (7) washing for five times, allowing the filter cake, with the rotation of the drum, to enter an unloading area II in the frame, and unloading gas to enter from an unloading area I in the control head to back flush the filter cake; unloading the filter cake to the pulping tank for pulping to obtain a slurry, and discharging the slurry.

The solvent exchanger in the step (1) comprises a frame and a control head; the frame is divided into a feeding section, a primary washing unit chamber, a secondary washing unit chamber, a tertiary washing unit chamber, a fourth washing unit chamber, a fifth washing unit chamber and an unloading section II by a separation block A, a separation block B, a separation block C, a separation block D, a separation block E, a separation block F and a separation block G. The control head is divided into a mother liquor chamber, a primary filtrate chamber, a secondary filtrate chamber, a tertiary filtrate chamber, a fourth filtrate chamber, a fifth filtrate chamber and an unloading section I by a separation block a, a separation block b, a separation block c, a separation block d, a separation block e, a separation block f and a separation block g. The separation block A, the separation block B, the separation block C, the separation block D, the separation block E, the separation block F and the separation block G are in one-to-one correspondence to the separation block a, the separation block b, the separation block c, the separation block d, the separation block e, the separation block f and the separation block g. An adjusting plate is arranged on the control head. A drainage opening is arranged at the end of the fifth filtrate chamber. The primary washing unit chamber, the secondary washing unit chamber, the tertiary washing unit chamber, the fourth washing unit chamber and the fifth washing unit chamber are respectively connected with the primary filtrate chamber, the secondary filtrate chamber, the tertiary filtrate chamber, the fourth filtrate chamber and the fifth filtrate chamber by the filtrate pipeline in a one-to-one correspondence manner.

The suction machine unit in the step (6) is one of centrifugal fan, ROOTS blower, vacuum pump or other unit with a suction machine action.

Compared with the prior art, the invention has the following advantages:
1 A suction machine unit, a bias flow filtrate tank and a bias flow filtrate pump are added in the invention. Upon the last washing, the residual filtrate in the filtrate pipeline is pumped to the bias flow filtrate tank by using differential pressure, and then is used again, which prevents the filtrate from entering the unloading section and discharging from an unloading port together with the back flushing gas for unloading to pollute the filter cake that has been washed clean, which not only improves the solvent exchange efficiency, but only reduces the overall demand of the system for washing liquor.

2 The control head of the invention is divided into a mother liquor chamber, a plurality of filtrate chambers and an unloading section I by a plurality of separation blocks. Therefore, by adjusting positions of separation blocks of the control head, the residual filtrate in the filtrate pipeline can be discharged into corresponding chambers during solvent exchange, and the filtrate will not enter the low-concentration washing liquor at the next stage, which improves the solvent exchange efficiency.

3 The control head of the invention is adjustable, which can ensure that different bias flow angles can be adjusted more flexibly and conveniently without changing equipment under different working conditions.

4 By improvements in both the technological process and the equipment structure, the invention significantly reduces consumption of process water, improves the solvent exchange efficiency and greatly reduces the energy consumption.

The invention will be described in detail in combination with drawings and preferred embodiments, but the drawings and preferred embodiments do not limit the invention.

Figure 1:
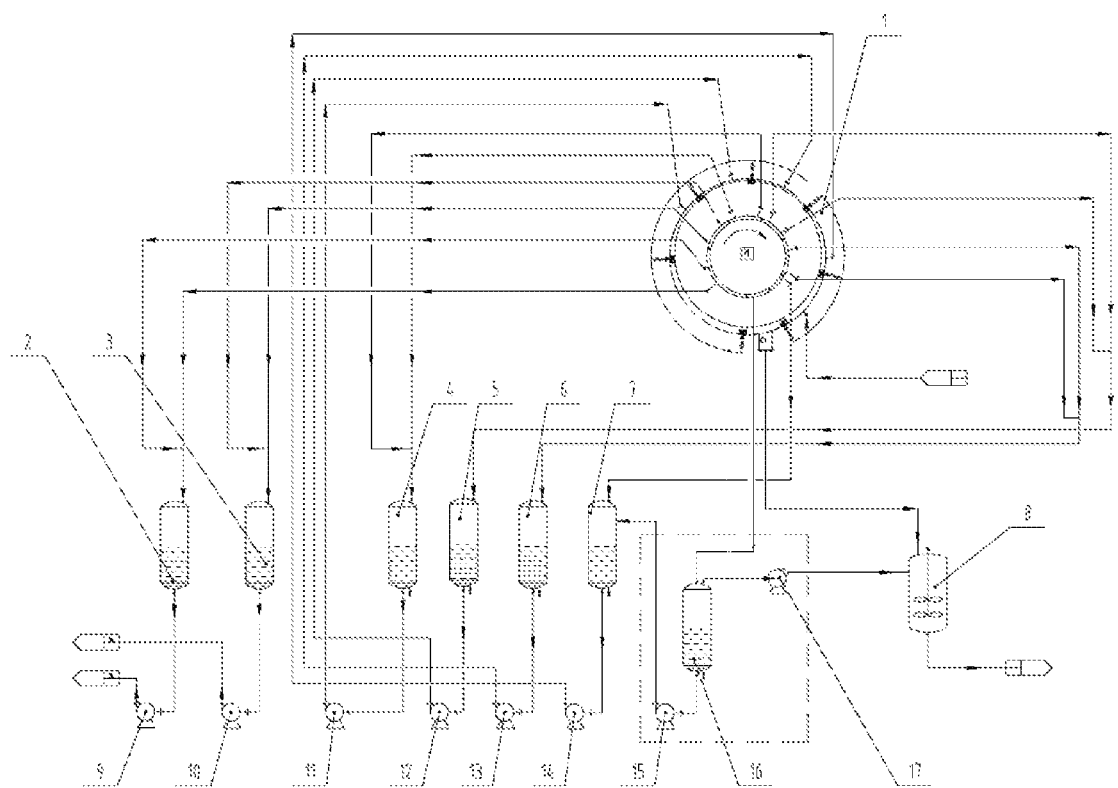
FIG. 1 is a schematic diagram of a solvent exchange process of the invention.

MARKS IN THE DRAWINGS
1—Solvent exchanger
2—Mother liquor tank
3—Primary filtrate tank
4—Secondary filtrate tank
5—Tertiary filtrate tank
6—Fourth filtrate tank
7—Fifth filtrate tank
8—Pulping tank
9—Mother liquor pump
10—Primary filtrate pump
11—Secondary filtrate pump
12—Tertiary filtrate pump
13—Fourth filtrate pump
14—Fifth filtrate pump
15—Bias flow filtrate pump
16—Bias flow filtrate tank
17—Suction machine unit
18—Frame
19—Feeding section
20—Mother liquor chamber
21—Separation block A
22—Separation block a
23—Control head
24—Primary washing unit chamber
25—Separation block B
26—Primary filtrate chamber
27—Secondary washing unit chamber
28—Separation block b
29—Secondary filtrate chamber
30—Separation block C
31—Separation block c
32—Tertiary filtrate chamber
33—Tertiary washing unit chamber
34—Filtrate pipeline
35—Separation block D
36—Separation block d
37—Fourth washing unit chamber
38—Fourth filtrate chamber
39—Separation block e
40—Separation block E
41—Fifth filtrate chamber
42—Fifth washing unit chamber
43—Separation block f
44—Separation block F
45—Unloading section I
46—Unloading section II
47—Separation block g
48—Separation block G
49—Adjusting plate
50—Drainage opening.

DETAILED DESCRIPTION OF THE INVENTION

The invention is described in detail in combination with drawings and preferred embodiments so as to further understand the purpose, solution and effect of the invention, but the drawings and preferred embodiments do not limit the protection scope of appended claims of the invention.

As shown in FIG. 1, a method for improving the exchange efficiency of a CTA solvent comprises following steps.

(1) A CTA slurry in a CTA slurry tank is pressurized into a solvent exchanger 1 by a slurry pump, passes through a feeding section 19 in a frame 18 of the solvent exchanger 1, and then enters a filter unit chamber for separation, so as to obtain respectively a mother liquor, a bias flow mother liquor and a suspended matter A. Both of the mother liquor and the bias flow mother liquor pass through a mother liquor chamber 20 in a control head 23 of the solvent exchanger 1 and enter a mother liquor tank 2, and are then discharged by a mother liquor pump 9 connected with the mother liquor tank 2.

Here, the bias flow mother liquor is from the residual mother liquor in a filtrate pipeline. The position of a separation block a22 between the mother liquor chamber 20 and a primary filtrate chamber 26 is adjusted to allow the separation block a 22 to lead a separation block A21 of the corresponding frame 18 by an angle θ1, and to allow the residual mother liquor to enter the corresponding mother liquor chamber 20 during the time in which drum rotates by the angle θ1.

Figure 2:
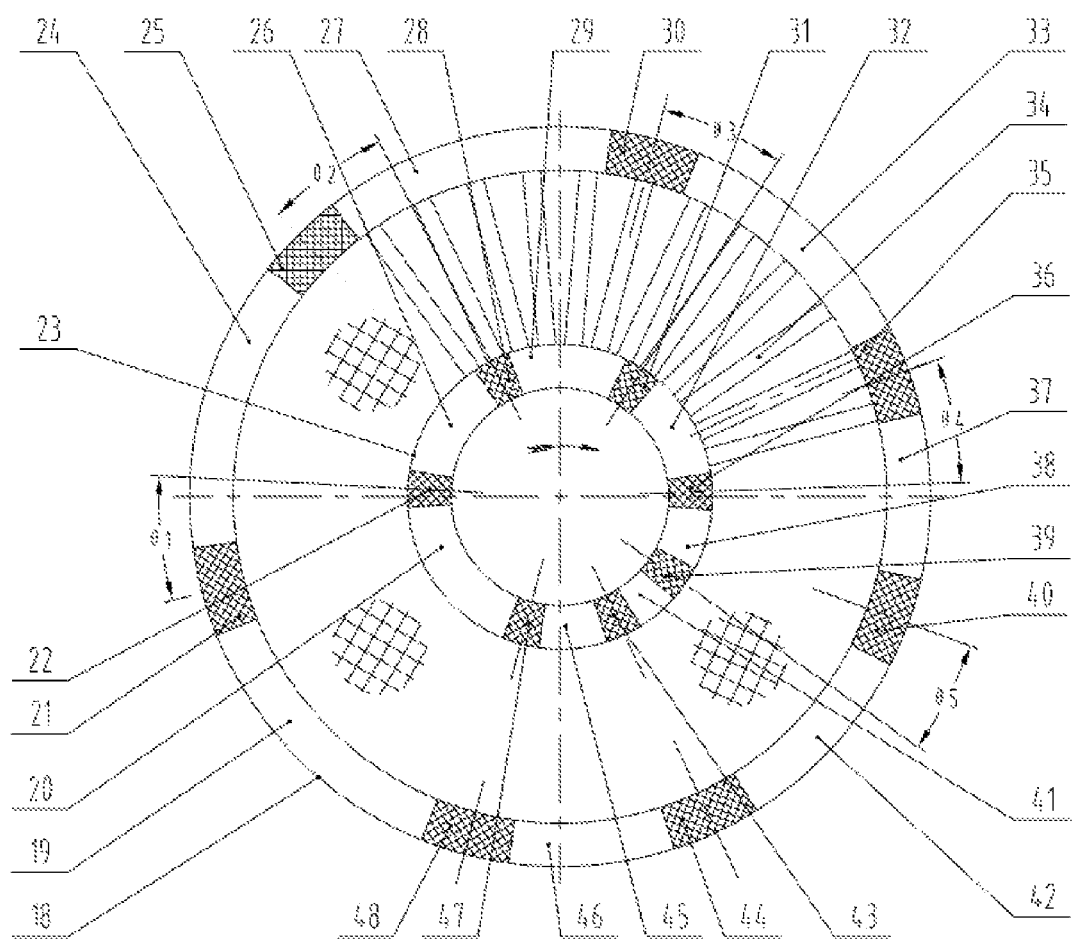
FIG. 2 is a simplified schematic diagram of a solvent exchanger of the invention.
Figure 3:
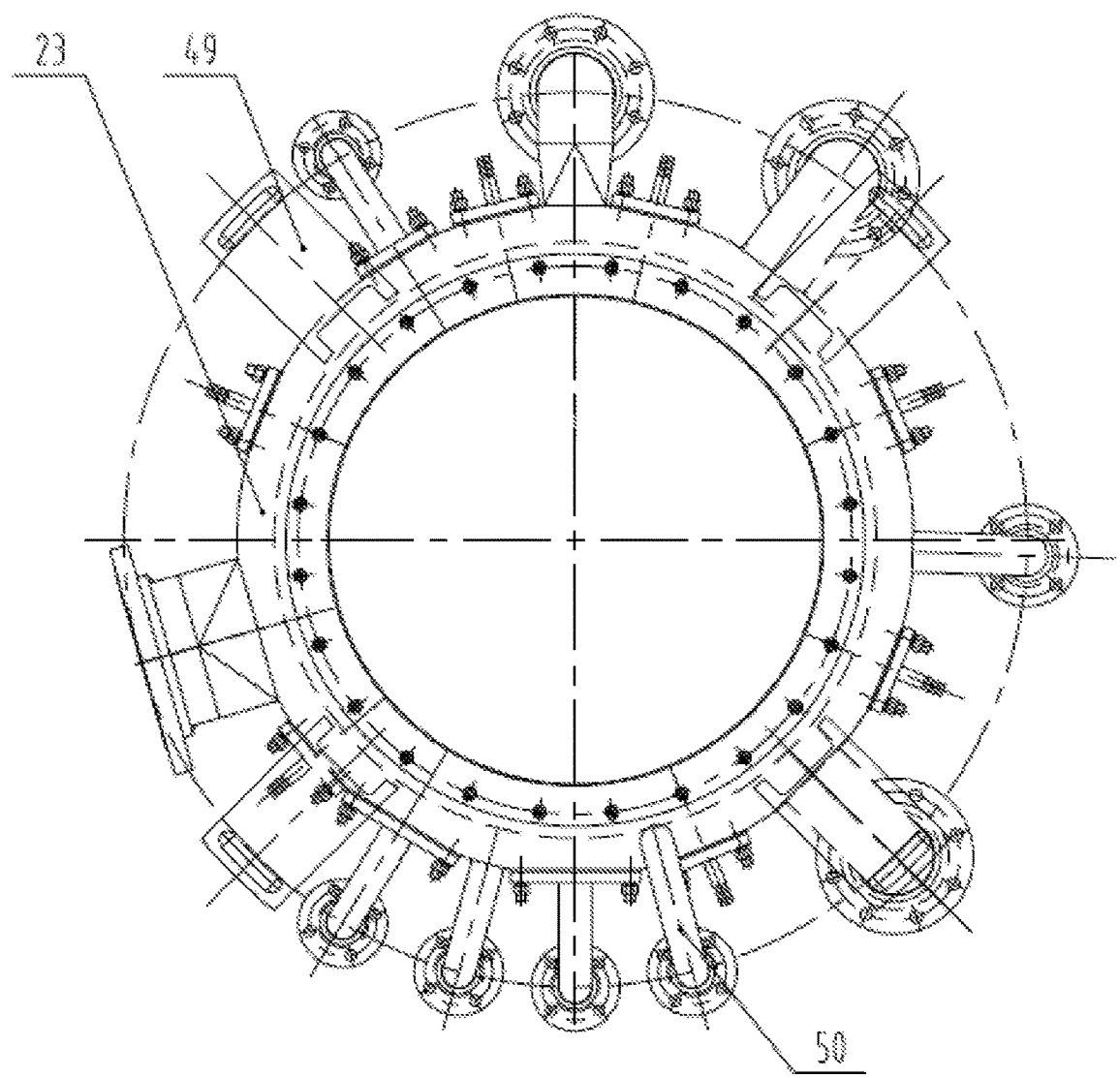
FIG. 3 is an outline drawing of a control head of the invention.

The solvent exchange 1 comprises a frame 18 and a control head 23 (see FIG. 2 and FIG. 3). The frame 18 is divided into a feeding section 19, a primary washing unit chamber 24, a secondary washing unit chamber 27, a tertiary washing unit chamber 33, a fourth washing unit chamber 37, a fifth washing unit chamber 42 and an unloading section II 46 by a separation block A 21, a separation block B 25, a separation block C 30, a separation block D 35, a separation block E 40, a separation block F 44 and a separation block G 48. The control head 23 is divided into a mother liquor chamber 20, a primary filtrate chamber 26, a secondary filtrate chamber 29, a tertiary filtrate chamber 32, a fourth filtrate chamber 38, a fifth filtrate chamber 41 and an unloading section I 45 by a separation block a22, a separation block b28, a separation block c31, a separation block d36, a separation block e39, a separation block f43 and a separation block g47. The separation block A21, the separation block B25, the separation block C30, the separation block D35, the separation block E40, the separation block F44 and the separation block G48 are in one-to-one correspondence to the separation block a22, the separation block b28, the separation block c31, the separation block d36, the separation block e39, the separation block f43 and the separation block g47. An adjusting plate 49 is arranged on the control head 23. A drainage opening 50 is arranged at the end of the fifth filtrate chamber 41. The primary washing unit chamber 24, the secondary washing unit chamber 27, the tertiary washing unit chamber 33, the fourth washing unit chamber 37 and the fifth washing unit chamber 42 are respectively connected with the primary filtrate chamber 26, the secondary filtrate chamber 29, the tertiary filtrate chamber 32, the fourth filtrate chamber 38 and the fifth filtrate chamber 41 through the filtrate pipeline 34 in a one-to-one correspondence manner.

(2) After the filter unit chamber is filled with the suspended matter A, the washing water stored in a primary washing water tank is pressurized into a primary washing unit chamber 24 in the frame 18 by a primary washing water pump. At the same time, the suspended matter A is conveyed into the primary washing unit chamber 24 for washing, so as to obtain respectively a primary filtrate, a bias flow primary filtrate and a suspended matter B. Both of the primary filtrate and the bias flow primary filtrate pass through the primary filtrate chamber 26 in the control head 23 and enter a primary filtrate tank 3, and are then discharged through a primary filtrate pump 10 connected with the primary filtrate tank 3.

Here, the washing water in the primary washing water tank is from a secondary filtrate and a bias flow secondary filtrate discharged from a secondary washing unit chamber 27, and the bias flow primary filtrate is from the residual primary filtrate in the filtrate pipeline. The position of a separation block b28 between the primary filtrate chamber 26 and a secondary filtrate chamber 29 is adjusted to allow the separation block b28 to lead a separation block B25 of the corresponding frame 18 by an angle $\theta 2$, and to allow the residual primary filtrate to enter the corresponding primary filtrate chamber 26 during the time in which the drum rotates by the angle $\theta 2$.

(3) After the primary washing unit chamber 24 is filled with the suspended matter B, the washing water stored in a secondary washing water tank is pressurized into a secondary washing unit chamber 27 in the frame 18 by a secondary washing water pump. At the same time, with the rotation of the drum, the suspended matter B is conveyed into the secondary washing unit chamber 27 for washing, so as to obtain respectively a secondary filtrate, a bias flow secondary filtrate and a suspended matter C. Both of the secondary filtrate and bias flow secondary filtrate pass through the secondary filtrate chamber 29 in the control head 23 and enter a secondary filtrate tank 4, and then enter the solvent exchanger 1 by a secondary filtrate pump 11 connected with the secondary filtrate tank 4.

Herein, the washing water in the secondary washing water tank is from a tertiary filtrate and a bias flow tertiary filtrate discharged from a tertiary washing unit chamber 33, and the bias flow secondary filtrate is from the residual secondary filtrate in the filtrate pipeline. The position of a separation block c31 between the secondary filtrate chamber 29 and a tertiary filtrate chamber 32 is adjusted to allow the separation block c31 to lead a separation block C30 of the corresponding frame 18 by an angle $\theta 3$, and to allow the residual secondary filtrate to enter the corresponding secondary filtrate chamber 29 during the time in which the drum rotates by the angle $\theta 3$.

(4) After the secondary washing unit chamber 27 is filled with the suspended matter C, the washing water stored in a tertiary washing water tank is pressurizing into a tertiary washing unit chamber 33 in the frame 18 by a tertiary washing water pump. At the same time, with the rotation of the drum, the suspended matter C is conveyed into the tertiary washing unit chamber 33 for washing, so as to obtain respectively a tertiary filtrate, a bias flow tertiary filtrate and a suspended matter D. Both of the tertiary filtrate and bias flow tertiary filtrate pass through the tertiary filtrate chamber 32 in the control head 23 and enter a tertiary filtrate tank 5, and then enter the solvent exchanger 1 by a tertiary filtrate pump 12 connected with the tertiary filtrate tank 5.

Here, the washing water in the tertiary washing water tank is from a fourth filtrate and a bias flow fourth filtrate discharged from a fourth washing unit chamber 37, and the bias flow tertiary filtrate is from the residual tertiary filtrate in the filtrate pipeline. The position of a separation block d36 between the tertiary filtrate chamber 32 and a fourth filtrate chamber 38 is adjusted to allow the separation block d36 to lead a separation block D35 of the corresponding frame 18 by an angle $\theta 4$, and to allow the residual tertiary filtrate to enter the corresponding tertiary filtrate chamber 32 during the time in which the drum rotates by the angle $\theta 4$.

(5) After the tertiary washing unit chamber 33 is filled with the suspended matter D, the washing water stored in a fourth washing water tank is pressurizing into a fourth washing unit chamber 37 in the frame 18 by a fourth washing water pump; At the same time, with the rotation of the drum, the suspended matter D is conveyed into the fourth washing unit chamber 37 for washing, so as to obtain respectively a fourth filtrate, a bias flow fourth filtrate and a suspended matter E. Both of the fourth filtrate and the bias flow fourth filtrate pass through the fourth filtrate chamber 38 in the control head 23 and enter a fourth filtrate tank 6, and is then conveyed into the solvent exchanger 1 by a fourth filtrate pump 13 connected with the fourth filtrate tank 6.

Here, the washing water in the fourth washing water tank is from a fifth filtrate and a bias flow fifth filtrate discharged from a fifth washing unit chamber 42, and the bias flow fourth filtrate is from the residual fourth filtrate in the filtrate pipeline. The position of a separation block e39 between the fourth filtrate chamber 38 and a fifth filtrate chamber 41 is adjusted to allow the separation block e39 to lead a separation block E40 of the corresponding frame 18 by an angle $\theta 5$, and to allow the residual fourth filtrate to enter the corresponding fourth filtrate chamber 38 during the time in which the drum rotates by the angle $\theta 5$.

(6) After the fourth washing unit chamber 37 is filled with the suspended matter E, the washing water stored in a fifth washing water tank is pressurizing into a fifth washing unit chamber 42 in the frame 18 by a fifth washing water pump. At the same time, with the rotation of the drum, the suspended matter E is conveyed into the fifth washing unit chamber 42 for washing, so as to obtain respectively a fifth filtrate, a bias flow fifth filtrate and a filter cake. The fifth filtrate passes through the fifth filtrate chamber 41 in the control head 23 and enters a fifth filtrate tank 7, and is then conveyed into the solvent exchanger 1 by a fifth filtrate pump 14 connected with the fifth filtrate tank 7. Here, the bias flow fifth filtrate is from the residual fifth filtrate in the filtrate pipeline, which is guided, by a suction machine unit 17, from a drainage opening 50 to a bias flow filtrate tank 16 through the fifth filtrate chamber 41, and is then conveyed into the fifth filtrate tank 7 by a bias flow filtrate pump 15 connected with the bias flow filtrate tank 16. An outlet of the suction machine unit 17 is connected with a pulping tank 8 to ensure no escape of tail suction machine gas. The washing water in the fifth washing water tank is from fresh water heated to 90° C.

Here, the suction machine unit 17 is one of centrifugal fan, ROOTS blower, vacuum pump or other units having a suction function.

(7) After the washing is performed for five times, with the rotation of the drum, the filter cake enters an unloading area II 46 in the frame 18. At the same time, unloading gas enters from an unloading area I 45 in the control head 23 to back flush the filter cake. Then, the filter cake is unloaded to the pulping tank 8 for pulping, so as to obtain a slurry and to discharge the slurry.

Of course, the invention may have other multiple embodiments. Those skilled in the art can make various corresponding changes and modifications according to the invention without departing from the spirit and essence of the invention, but these changes and modifications should be incorporated in the protection scope of the claims appended to the invention.

INDUSTRIAL APPLICABILITY

The present invention additionally provides a suction machine unit, a bias flow filtrate tank and a bias flow filtrate pump, for pumping the residual filtrate in the filtrate pipeline into the bias flow filtrate tank by means of differential pressure during the last washing, for the later use. In this way, such residual filtrate is prevent from entering the unloading section, being discharged from an unloading entrance together with the back flushing gas for unloading, and polluting the filter cake that has been washed clean. Therefore, the present invention may not only improve the solvent exchange efficiency, but also reduce the total amount of necessary washing liquor in the system. The control head of the solvent exchanger is divided into a mother liquor chamber, a plurality of filtrate chambers and an unloading section I by a plurality of separation blocks. The positions of the separation blocks in the control head may be adjusted to allow the residual filtrate in the filtrate pipeline to be discharged into corresponding chambers during solvent exchange, without entering the low-concentration washing liquor at the next stage. In this way, the solvent exchange efficiency may be improved. By improving in both the process flow and the equipment structure, the invention significantly reduces the water consumption in the process, improves the solvent exchange efficiency, and greatly reduces the energy consumption.

What is claimed is:

1. A method for improving the exchange efficiency of a CTA solvent, comprising the following steps:

(1) pressurizing, by a slurry pump, a CTA slurry in a CTA slurry tank into a solvent exchanger, and passing the CTA slurry through a feeding section in a frame of the solvent exchanger to a filter unit chamber for separation, to obtain respectively a mother liquor, a bias flow mother liquor and a suspended matter A, both of the mother liquor and the bias flow mother liquor passing through a mother liquor chamber in a control head of the solvent exchanger and entering a mother liquor tank, and then being discharged by a mother liquor pump connected with the mother liquor tank, wherein the bias flow mother liquor is from a residual mother liquor in a filtrate pipeline; and wherein the position of a separation block a between the mother liquor chamber and a primary filtrate chamber is adjusted to allow the separation block a to lead a corresponding separation block A in the frame by an angle θ1, and to allow the residual mother liquor to enter the corresponding mother liquor chamber during the time in which a drum rotates by the angle θ1;

(2) after the filter unit chamber is filled with the suspended matter A, pressurizing, by a primary washing water pump, washing water stored in a primary washing water tank into a primary washing unit chamber in the frame, and conveying the suspended matter A into the primary washing unit chamber for washing, to obtain respectively a primary filtrate, a bias flow primary filtrate and a suspended matter B, both of the primary filtrate and the bias flow primary filtrate passing through the primary filtrate chamber in the control head and entering a primary filtrate tank, and then being discharged by a primary filtrate pump connected with the primary filtrate tank, wherein the washing water in the primary washing water tank is from a secondary filtrate and a bias flow secondary filtrate discharged from a secondary washing unit chamber, and the bias flow primary filtrate is from a residual primary filtrate in the filtrate pipeline, and wherein the the position of a separation block b between the primary filtrate chamber and a secondary filtrate chamber is adjusted to allow the separation block b to lead a separation block B of the corresponding frame by an angle θ2, and to allow the residual primary filtrate to enter the corresponding primary filtrate chamber during the time in which the drum rotates by the angle θ2;

(3) after the primary washing unit chamber is filled with the suspended matter B, pressurizing, by a secondary washing water pump, washing water stored in a secondary washing water tank into a secondary washing unit chamber in the frame, and at the same time, with the rotation of the drum, conveying the suspended matter B into the secondary washing unit chamber for washing, to obtain respectively a secondary filtrate, a bias flow secondary filtrate and a suspended matter C, both of the secondary filtrate and the bias flow secondary filtrate passing through the secondary filtrate chamber in the control head and entering a secondary filtrate tank, and then being conveyed into the solvent exchanger by a secondary filtrate pump connected with the secondary filtrate tank, wherein the washing water in the secondary washing water tank is from a tertiary filtrate and a bias flow tertiary filtrate discharged from a tertiary washing unit chamber, and the bias flow secondary filtrate is from a residual secondary filtrate in the filtrate pipeline; and wherein the position of a separation block c between the secondary filtrate chamber and a tertiary filtrate chamber is adjusted to allow the separation block c to lead a corresponding separation block C of the frame by an angle θ3, and to allow the residual secondary filtrate to enter the corresponding secondary filtrate chamber during the time in which the drum rotates by the angle θ3;

(4) after the secondary washing unit chamber is filled with the suspended matter C, pressurizing, by a tertiary washing water pump, washing water stored in a tertiary washing water tank into a tertiary washing unit chamber in the frame; at the same time, with the rotation of the drum, conveying the suspended matter C into the tertiary washing unit chamber for washing, to obtain respectively a tertiary filtrate, a bias flow tertiary filtrate and a suspended matter D, both of the tertiary filtrate and the bias flow tertiary filtrate passing through the tertiary filtrate chamber in the control head and entering a tertiary filtrate tank, and then being conveyed into the solvent exchanger by a tertiary filtrate pump connected with the tertiary filtrate tank, wherein the washing water in the tertiary washing water tank is from a fourth filtrate and a bias flow fourth filtrate discharged from a fourth washing unit chamber, and the bias flow tertiary filtrate is from a residual tertiary filtrate in the filtrate pipeline; and wherein the position of a separation block d between the tertiary filtrate chamber and a fourth filtrate chamber is adjusted to allow the separation block d to lead a corresponding separation block D of the frame by an angle $\theta 4$, and to allow the residual tertiary filtrate to enter the corresponding tertiary filtrate chamber during the time in which the drum rotates by the angle $\theta 4$;

(5) after the tertiary washing unit chamber is filled with the suspended matter D, pressurizing, by a fourth washing water pump, washing water stored in a fourth washing water tank into a fourth washing unit chamber in the frame; and at the same time, with the rotation of the drum, conveying the suspended matter D into the fourth washing unit chamber for washing, to respectively obtain a fourth filtrate, a bias flow fourth filtrate and a suspended matter E; both of the fourth filtrate and the bias flow fourth filtrate passing through the fourth filtrate chamber in the control head and entering a fourth filtrate tank, and then being conveyed into the solvent exchanger by a fourth filtrate pump connected with the fourth filtrate tank, wherein the washing water in the fourth washing water tank is from a fifth filtrate and a bias flow fifth filtrate discharged from a fifth washing unit chamber, and the bias flow fourth filtrate is from a residual fourth filtrate in the filtrate pipeline; and wherein the position of a separation block e between the fourth filtrate chamber and a fifth filtrate chamber is adjusted to allow the separation block e to lead a corresponding separation block E of the frame by an angle $\theta 5$, and to allow the residual fourth filtrate to enter the corresponding fourth filtrate chamber during the time in which the drum rotates by the angle $\theta 5$;

(6) after the fourth washing unit chamber is filled with the suspended matter E, pressurizing, by a fifth washing water pump, washing water stored in a fifth washing water tank into a fifth washing unit chamber in the frame; and at the same time, with the rotation of the drum, conveying the suspended matter E into the fifth washing unit chamber for washing, to obtain respectively a fifth filtrate, a bias flow fifth filtrate and a filter cake; the fifth filtrate passing through the fifth filtrate chamber in the control head and entering a fifth filtrate tank, and then being conveyed into the solvent exchanger by a fifth filtrate pump connected with the fifth filtrate tank, wherein the bias flow fifth filtrate is from a residual fifth filtrate in the filtrate pipeline; which is guided, by a suction machine unit, from a drainage opening to a bias flow filtrate tank through the fifth filtrate chamber, and is conveyed into the fifth filtrate tank by a bias flow filtrate pump connected with the bias flow filtrate tank, wherein an outlet of the suction machine unit is connected with a pulping tank, and the washing water in the fifth washing water tank is from fresh water heated to 90° C.; and (7) after the washing are completed for five times, allowing the filter cake, with the rotation of the drum, to enter an unloading section II in the frame between a separation block F and a separation block G, and allowing unloading gas to enter from an unloading section I in the control head between a separation block f and a separation block g for back-flushing the filter cake; and then unloading the filter cake into the pulping tank for pulping to obtain a slurry, and discharging.

2. The method for improving the exchange efficiency of a CTA solvent according to claim 1, wherein the solvent exchanger comprises the frame and the control head;

wherein the frame is divided into the feeding section, the primary washing unit chamber, the secondary washing unit chamber, the tertiary washing unit chamber, the fourth washing unit chamber, the fifth washing unit chamber and the unloading section II by the separation block A, the separation block B, the separation block C, the separation block D, the separation block E, the separation block F and the separation block G;

wherein the control head is divided into the mother liquor chamber, the primary filtrate chamber, the secondary filtrate chamber, the tertiary filtrate chamber, the fourth filtrate chamber, the fifth filtrate chamber and the unloading section I by the separation block a, the separation block b, the separation block c, the separation block d, the separation block e, the separation block f and the separation block g;

wherein the separation block A, the separation block B, the separation block C, the separation block D, the separation block E, the separation block F and the separation block G are in one-to-one correspondence to the separation block a, the separation block b, the separation block c, the separation block d, the separation block e, the separation block f and the separation block g;

wherein an adjusting plate is arranged on the control head;

wherein a drainage opening is arranged at the end of the fifth filtrate chamber; and wherein the primary washing unit chamber, the secondary washing unit chamber, the tertiary washing unit chamber, the fourth washing unit chamber and the fifth washing unit chamber are respectively connected with the primary filtrate chamber, the secondary filtrate chamber, the tertiary filtrate chamber, the fourth filtrate chamber and the fifth filtrate chamber by a filtrate pipeline in a one-to-one correspondence manner.

3. The method for improving the exchange efficiency of a CTA solvent according to claim 1, wherein the suction machine unit in the step (6) is one of a centrifugal fan, blower, vacuum pump or other units having a suction function.

* * * * *